United States Patent
Chawla et al.

(10) Patent No.: US 9,633,404 B2
(45) Date of Patent: Apr. 25, 2017

(54) METHOD AND SYSTEM FOR SECURE CO-BROWSING OF PATIENT RECORDS ON COMMUNICATION DEVICES

(71) Applicant: AGNITY HEALTHCARE, INC., Fremont, CA (US)

(72) Inventors: Sanjeev Chawla, Fremont, CA (US); Atul Varshneya, Cupertino, CA (US); Amit Kumar, Noida (IN)

(73) Assignee: AGNITY HEALTHCARE, INC., Fremont, CA (US)

( * ) Notice: Subject to any disclaimer, the term of this patent is extended or adjusted under 35 U.S.C. 154(b) by 18 days.

(21) Appl. No.: 14/391,378

(22) PCT Filed: Apr. 4, 2013

(86) PCT No.: PCT/US2013/035307
§ 371 (c)(1),
(2) Date: Oct. 8, 2014

(87) PCT Pub. No.: WO2013/154911
PCT Pub. Date: Oct. 17, 2013

(65) Prior Publication Data
US 2015/0106907 A1    Apr. 16, 2015

Related U.S. Application Data

(60) Provisional application No. 61/621,821, filed on Apr. 9, 2012.

(51) Int. Cl.
*G06F 7/04*    (2006.01)
*G06F 15/16*    (2006.01)
(Continued)

(52) U.S. Cl.
CPC ......... *G06Q 50/24* (2013.01); *H04L 63/0853* (2013.01); *H04L 65/1006* (2013.01);
(Continued)

(58) Field of Classification Search
CPC ...... G06F 15/16; G06F 19/321; G06F 19/322; G06Q 10/00; G06Q 50/22; G06Q 50/24
(Continued)

(56) References Cited

U.S. PATENT DOCUMENTS 6,574,742 B1    6/2003    Jamroga et al.
2002/0035485 A1*    3/2002    Mita .................... G06F 19/322
                                                                            705/2

(Continued)

OTHER PUBLICATIONS

International Search Report, International Application No. PCT/US2013/035307 dated Apr. 4, 2013.

*Primary Examiner* — Jayesh Jhaveri
(74) *Attorney, Agent, or Firm* — Arent Fox LLP (57) ABSTRACT

A method and system are provided for co-browsing of patient records on communication devices. The method includes setting up a communication session between a first communication device and one or more second communication devices, where the communication session is initiated by the first communication device. Further, the method includes accessing one or more patient records via a server, where the one or more patient records are accessed at the first communication device. The method further includes sending a reference of the one or more patient records to the one or more second communication devices, where the reference is sent from the first communication device.

30 Claims, 8 Drawing Sheets (51) Int. Cl.
  *G06F 17/30* (2006.01)
  *H04L 29/06* (2006.01)
  *G06Q 50/24* (2012.01)
  *G06Q 50/22* (2012.01)
  *G06Q 10/00* (2012.01)
  *G06F 19/00* (2011.01)

(52) U.S. Cl.
  CPC ............ *G06F 15/16* (2013.01); *G06F 19/321* (2013.01); *G06F 19/322* (2013.01); *G06Q 10/00* (2013.01); *G06Q 50/22* (2013.01)

(58) Field of Classification Search
  USPC .............................. 705/2; 709/227; 711/100
  See application file for complete search history.

(56) References Cited

U.S. PATENT DOCUMENTS

| | | | |
|---|---|---|---|
| 2004/0199580 A1 | 10/2004 | Zhakov et al. | |
| 2006/0143043 A1* | 6/2006 | McCallie, Jr. ......... | G06Q 10/10 705/2 |
| 2007/0033175 A1* | 2/2007 | Everett-Church | G06F 17/30864 |
| 2007/0061170 A1* | 3/2007 | Lorsch .................. | G06F 19/322 705/3 |
| 2011/0219419 A1* | 9/2011 | Reisman ........... | G06F 17/30873 725/112 |
| 2011/0225003 A1* | 9/2011 | McCallie, Jr. ......... | G06Q 10/10 705/2 |
| 2011/0302237 A1* | 12/2011 | Knight ................. | G06Q 10/101 709/203 |
| 2013/0054481 A1* | 2/2013 | Upadhyaya ............ | G06Q 50/01 705/319 |

\* cited by examiner

METHOD AND SYSTEM FOR SECURE CO-BROWSING OF PATIENT RECORDS ON COMMUNICATION DEVICES

RELATED APPLICATIONS

This present application is a National Stage entry of International Application No. PCT/US2013/035307, filed Apr. 4, 2013, which claims priority to U.S. Provisional Patent Application No. 61/621,821, filed Apr. 9, 2012. The disclosures of the prior applications are incorporated in their entirety reference.

BACKGROUND

1. Field

The present invention relates to co-browsing in general. More specifically, the present invention relates to a method and system for secure co-browsing of patient records on communication devices.

2. Background

Increasingly, mobile devices are becoming the devices of choice for users, for work as well as for personal use. Examples of such personal use include, but are not limited to, reading emails, reading news, finance information, weather forecasts, banking, and playing games. Examples of work use include, but are not limited to, tracking a sales force, sharing documents, sending emails. A lot of times, users desire to co-browse the same data files. Co-browsing includes joint navigation of the same data files or other resources substantially contemporaneously by multiple users. Co-browsing can be for personal use such as sharing a web site, ecommerce shopping, photo sharing, video sharing, social networking applications, as well as professional use such as sharing presentations, discussing documents, sharing an ecommerce page with a customer, distance learning, sharing patient records and the like.

Very often, physicians and nurses have to co-browse together to make decisions about the course of treatment for patients. By the nature of their jobs they are not always physically present when such need arises, which can be at any time of the day or night. Being able to share patient charts, such as objective information about the patient, during an audio or video call, greatly improves the time to take the decisions, as well as the quality of the decisions themselves. Such medical professionals can benefit from co-browsing by being able to view a same patient record during discussions. This improves the delivery of care both in quality (better care) and quantity (serve more patients).

It is important to note that the nature of data that is shared via co-browsing by physicians and nurses is not very dynamic in nature. Namely, the data is not generated on-the-fly during the co-browsing session, the data shared are the medical records of the patient are fairly static and stored on the electronic medical records systems. However, the patient data records themselves that are required to be shared and discussed by the physicians and nurses can be numerous within a single co-browsing session. Further, nowadays mobile devices, such as smartphones and tablets, are widely used among physicians and nurses.

Therefore mobile devices would be an ideal candidate for the co-browsing of patient data records.

One of the major challenges for providing co-browsing on mobile devices is that the mobile devices have limited computing resources. Therefore such devices are not well equipped to support co-browsing along with audio and video communications. Further, taking into account the fact that mobile devices have diverse operating systems browsers, and that co-browsing requires special permissions and capabilities from the operating systems, and access to the workings of those browsers. Implementing co-browsing on mobile devices has presented an unsolved challenge to state of the art systems Accordingly, there remains a need for a method and system for providing co-browsing of patient records, which can be performed using mobile devices with limited computing resources. Further, there is a need for a method and system that can work across diverse kinds of mobile devices. Still further, there is a need for a method and system which does not require special permissions and capabilities from the operating systems of mobile devices. Thus, there is a need for a method and system that can provide co-browsing of patient records using low computing resources on communication devices.

SUMMARY

Accordingly, it is an object of the present invention to provide a method and system for providing co-browsing of patient records capability on communication devices.

And accordingly, it is another object of the present invention to provide a method and system for providing co-browsing capability in a secure way on communication devices with limited computing resources. And accordingly, it is another object of the present invention to provide a method and system for providing secure co-browsing of patient records capability on communication devices.

It is yet another object of the present invention to provide a method and system for providing secure co-browsing without depending on persistently storing sensitive patient data outside of clinical information systems such as electronic medical records (EMRs), electronic health records (EHRs) and personal health records (PHRs).

The above and other objects of the present invention are achieved by providing a method and system for providing co-browsing of patient records on communication devices without using a lot of computing resources. The method includes setting up a communication session between a first communication device and one or more second communication devices, where the communication session is initiated by the first communication device. Further, the method includes accessing one or more patient data records from a server, where the one or more patient data records are accessed on the first communication device. The method further includes sending a reference of the one or more patient data records to the one or more second communication devices, where the reference is sent from the first communication device. Further, the method includes requesting the server to access the one or more patient data records from at least one of the one or more communication devices, where the request includes the reference of the one or more patient data records. Finally, the method includes invoking co-browsing for the one or more patient data records, where the co-browsing is provided during the communication session. The method eliminates the need to persistently store the sensitive patient data outside of the clinical information systems such as EMRs, EHRs, and PHRs, that securely manage the patient data. Also, the method encrypts the data when in transit over any network.

BRIEF DESCRIPTION OF THE DRAWINGS

For a more complete understanding of the present invention, the needs satisfied thereby, and the objects, features, and advantages thereof, reference now is made to the following description taken in connection with the accompanying drawings.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail the particular method and system for co-browsing of patient records on communication devices in accordance with an embodiment of the present invention, it should be observed that the present invention resides primarily in combinations of method and system components related to communication device of the present invention.

Accordingly, the system components have been represented where appropriate by conventional symbols in the drawings, showing only those specific details that are pertinent to understanding the present invention so as not to obscure the disclosure with details that will be readily apparent to those of ordinary skill in the art having the benefit of the description herein.

In this document, relational terms such as 'first' and 'second', and the like may be used solely to distinguish one entity or action from another entity or action without necessarily requiring or implying any actual such relationship or order between such entities or actions. The terms 'comprises', 'comprising', or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by 'comprises . . . a' does not, without more constraints, preclude the existence of additional identical elements in the process, method, article, or apparatus that comprises the element.

The terms "computing device" and "communication device" have been used interchangeably, and refer to computing device which has the capability of communicating or interacting with its users.

While the present invention has been described in connection with preferred embodiments, it will be understood by those skilled in the art that variations and modifications of the preferred embodiments described above may be made without departing from the scope of the invention. Other embodiments will be apparent to those skilled in the art from a consideration of the specification or from a practice of the invention disclosed herein. It is intended that the specification and the described examples are considered exemplary only, with the true scope of the invention indicated by the following claims.

A method is provided for co-browsing of patient records on a plurality of communication devices, in accordance with an embodiment of the present invention. Co-browsing of patient records includes joint navigation of the same patient data record files at the same time by multiple users. The method includes setting up a communication session between a first communication device and one or more second communication devices, where the communication session is initiated by the first communication device. Further, the method includes accessing one or more patient data records from a server, where the one or more patient data records are accessed on the first communication device. The method further includes sending a reference of the one or more patient data records to the one or more second communication devices, where the reference is sent from the first communication device. Further, the method includes requesting the server to access the one or more patient data records from at least one of the one or more communication devices, where the request includes the reference of the one or more patient data records. Finally, the method includes invoking co-browsing for the one or more patient data records, where the co-browsing is provided during the communication session.

Figure 1:
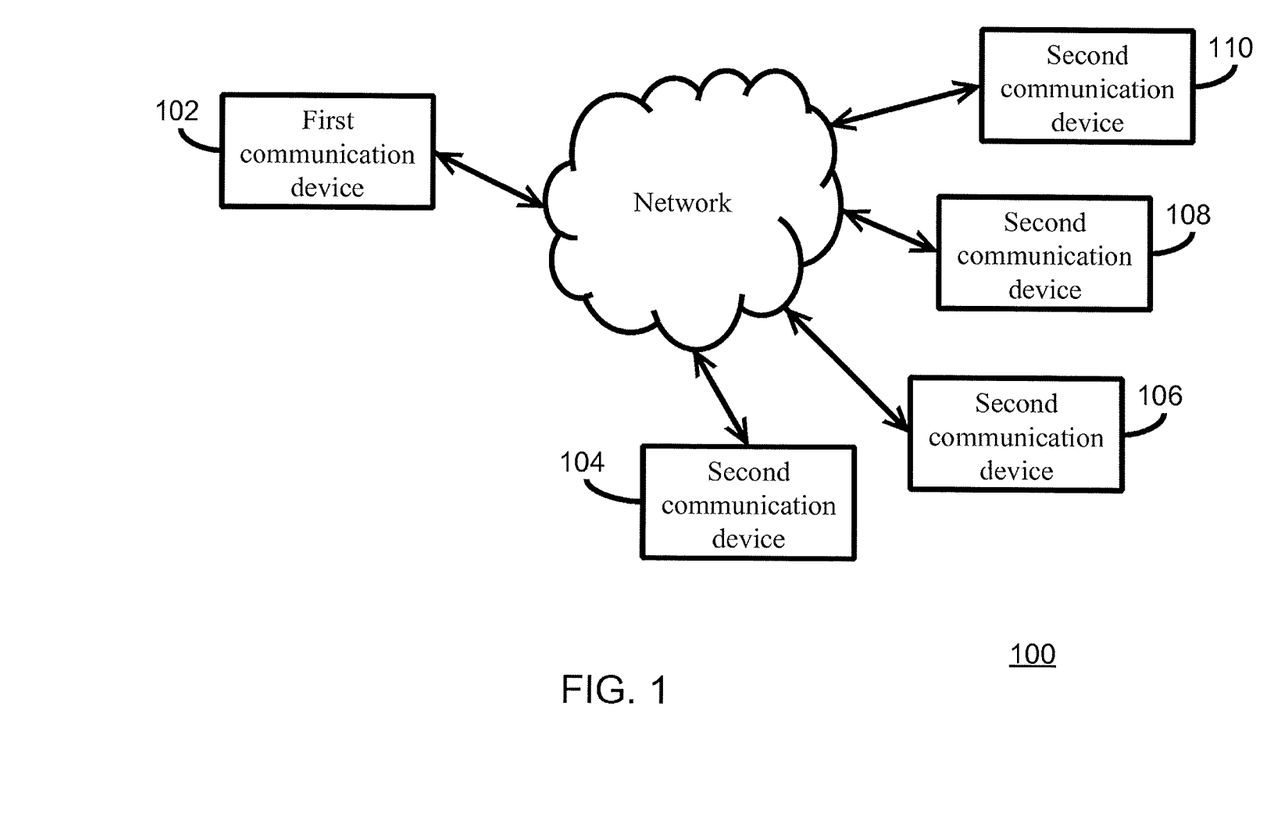
FIG. 1 shows an environment 100 in which various embodiments of the present invention can be practiced.

FIG. 1 shows an environment 100 in which various embodiments of the present invention can be practiced. The environment 100 includes a first communication device 102 and a one or more second communication devices 104, 106, 108 and 110. Examples of the communication devices include, but are not limited to, a desktop computer, a laptop, a mobile phone, a tablet PC, a netbook, an e-book reader and a PDA. In the present invention, at least one of the communication devices is a communication device with low computing resources. Examples of communication devices with low computing resources include, but are not limited to, a mobile phone, a smartphone, a tablet PC and an embedded device. The first communication device 102 and the one or more second communication devices 104, 106, 108 and 110 are connected via a network. The network is one or more of a 2G network, a 3G network, a 4G network, an Internet network, and a local area network (LAN).

Figure 2:
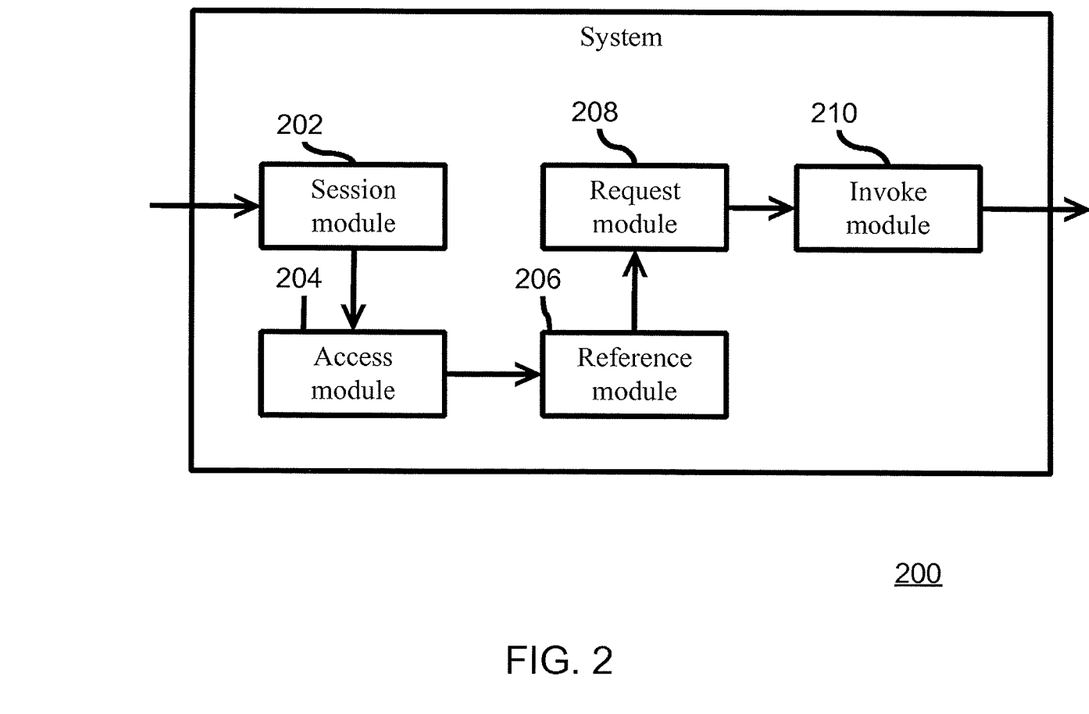
FIG. 2 shows a block diagram of a system for co-browsing of patient records on communication devices, in accordance with an embodiment of the present invention.

FIG. 2 shows a block diagram of a system 200 for co-browsing of patient records on communication devices, in accordance with an embodiment of the present invention. The system 200 includes a session module 202, an access module 204, a reference module 206, a request module 208, and an invoke module 210. The session module 202 sets up a communication session between a first communication device 102 and one or more second communication devices 104, 106, 108 and 110, where the communication session is initiated by the first communication device 102. In an embodiment of the present invention, the communication session is one of a voice call and a video call. The communication session can take place over one of a Plain Old Telephone Service (POTS) network, a 2G network, a 3G network, a VoIP network, a 4G network and a local area network (LAN). The communication session takes place using a communication protocol of establishing communication sessions among communication end-points. Examples of the communication protocol include, but are not limited to, Session Initiation Protocol (SIP), Extensible Messaging and Presence Protocol (XMPP), Session Description Protocol (SDP), Inter-Asterisk exchange (IAX), H.323 protocol, Media Gateway Control Protocol (MGCP), Signaling System #7 (SS7), Integrated Services Digital Network (ISDN), POTS protocol and a voice over Internet Protocol (VoIP) protocol.

The access module 204 accesses one or more patient data records from a server, where the one or more patient data records are accessed on the first communication device 102. The patient data records can include one or more of demographic data, medical history, family history, imaging reports, laboratory test results, medications, dosing, prescription records, surgeries records, vaccination data, observations of daily living (ODLs), Xray, MRI or other imaging records and clinical information. Further, the one or more patient records are part of one of an EMR, an EHR and a PHR. In an embodiment of the present invention, the server is one of a web server, a server cloud, a proxy server, a local server and a LAN server. Further, the server provides access the one or more patient data records by being one or more of a proxy of the patient data records, an adaptor of the patient data records, and an aggregator of the patient data records. Examples of the patient data records include, but are not limited to, EMRs and EHRs.

The reference module 206 sends a reference of the one or more patient data records to the one or more second communication devices 104, 106, 108 and 110, where the reference is sent by the first communication device 102. In an embodiment of the present invention, the reference is sent by the first communication device 102 to the at least one of the one or more second communication devices 104, 106, 108 and 110 via one of a signaling message, a push notification, a multi-media message (MMS), a SMS and an Email. The request module 208 then requests the server to access the one or more patient data records from at least one of the one or more second communication devices 104, 106, 108 and 110, where the request includes the reference of the one or more patient data records. In an embodiment of the present invention, the reference includes one or more of a link to the patient data records, a data record ID, authentication information and a session token. Finally, the invoke module 210 invokes co-browsing for the one or more patient data records, where the co-browsing is provided during the communication session.

Figure 3:
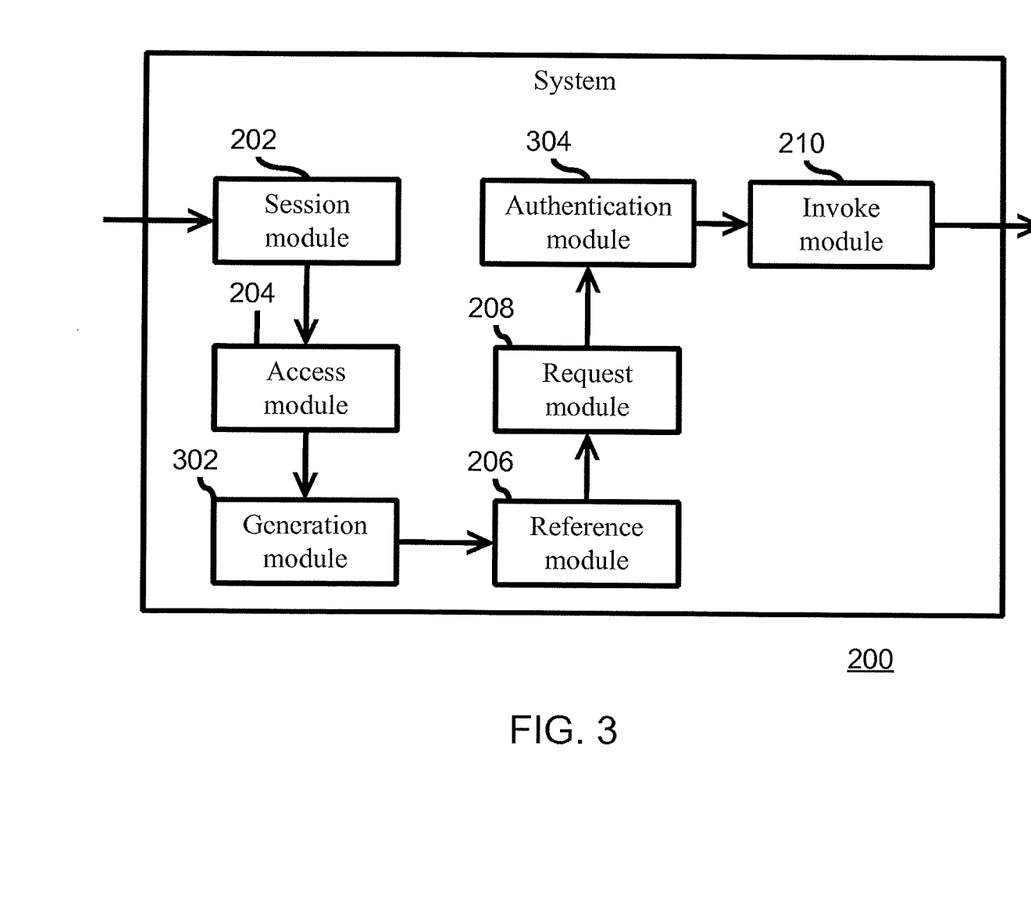
FIG. 3 shows a block diagram of a system for co-browsing of patient records on communication devices, in accordance with another embodiment of the present invention.

FIG. 3 shows a block diagram of a system 200 for co-browsing of patient records on communication devices, in accordance with another embodiment of the present invention. The system 200 includes the session module 202, the access module 204, a generation module 302, the reference module 206, the request module 208, an authentication module 304 and the invoke module 210. The session module 202 sets up a communication session between a first communication device 102 and one or more second communication devices 104, 106, 108 and 110, where the communication session is initiated by the first communication device 102.

In an embodiment of the present invention, the communication session is one of a voice call and a video call. The access module 204 accesses one or more patient data records from a server, where the one or more patient data records are accessed on the first communication device 102. In an embodiment of the present invention, the system 200 includes a device authentication module. The device authentication module 306 authenticates the first communication device 102 before providing an access to the one or more patient data records, where the authentication is performed by the server. The generation module 302 then generates a reference of the one or more patient data records, where the reference is generated by the server. The reference is then sent by the server to the first communication device 102. The reference module 206 sends the reference of the one or more patient data records to the one or more second communication devices 104, 106, 108 and 110, where the reference is sent by the first communication device 102.

In an embodiment of the present invention, the reference is sent by the first communication device 102 to the at least one of the one or more second communication devices 104, 106, 108 and 110 via one of a signaling message, a push notification, a multi-media message (MMS), a SMS and an Email. The request module 208 then requests the server to access the one or more patient data records from at least one of the one or more second communication devices 104, 106, 108 and 110, where the request includes the reference of the one or more patient data records.

In an embodiment of the present invention, the reference includes one or more of a link to the patient data records, a data record ID, authentication information and a session token. The authentication module 304 authenticates the reference received from the at least one of the one or more second communication devices 104, 106, 108 and 110, where the authentication is performed at the server. Finally, the invoke module 210 invokes co-browsing for the one or more patient data records, where the co-browsing is provided during the communication session. In an embodiment of the present invention, the co-browsing is one of synchronous co-browsing and asynchronous co-browsing between the first communication device 102 and the at least one of the one or more second communication devices 104, 106, 108 and 110.

In an embodiment of the present invention, the system 200 includes an exit module for closing the access to the one or more patient data records to the at least one of the one or more second communication devices 104, 106, 108 and 110 when the communication session is closed.

In another embodiment of the present invention, the system 200 includes a post-session module for continuing providing the access to the patient data records to the at least one of the one or more second communication devices 104, 106, 108 and 110 after the communication session is closed.

Figure 4:
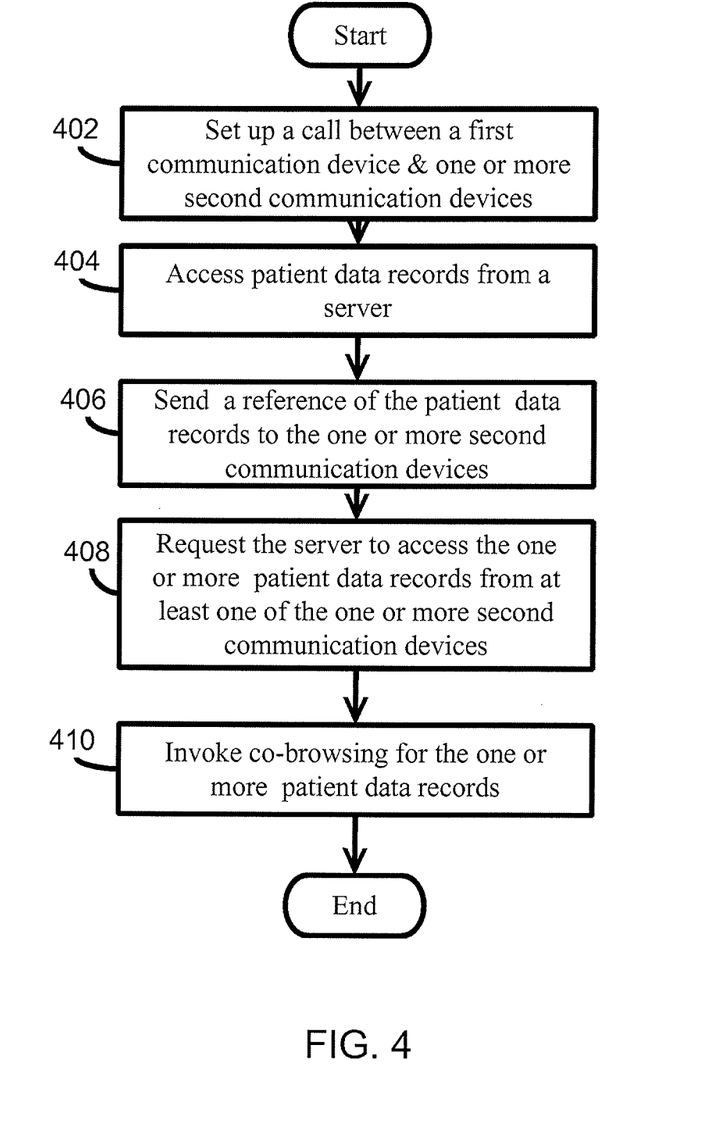
FIG. 4 shows a flow chart of a method for co-browsing of patient records on communication devices, in accordance with an embodiment of the present invention.

FIG. 4 shows a flow chart of a method for co-browsing of patient records on communication devices, in accordance with an embodiment of the present invention. At step 402, the system 200 sets up a communication session between the first communication devices 102 and the one or more second communication devices 104, 106, 108 and 110, where the communication is initiated by the first communication device 102. At step 404, the first communication device 102 accesses one or more patient data records on a server. In an embodiment of the present invention, the server provides a reference of the one or more patient data records to the first communication device 102. In another embodiment of the present invention, the first communication device 102 already has a reference of the one or more patient data records. At step 406, the first communication device 102 sends the reference of the one or more patient data records to the one or more second communication devices 104, 106,

108 and 110. At step 408, at least one of the one or more second communication devices 104, 106, 108 and 110 requests the server to access the one or more patient data records, where the request includes the reference of the one or more patient data records. Finally, at step 410, the system 200 invokes the co-browsing for the one or more patient data records, where the co-browsing is provided during the communication session.

Figure 5:
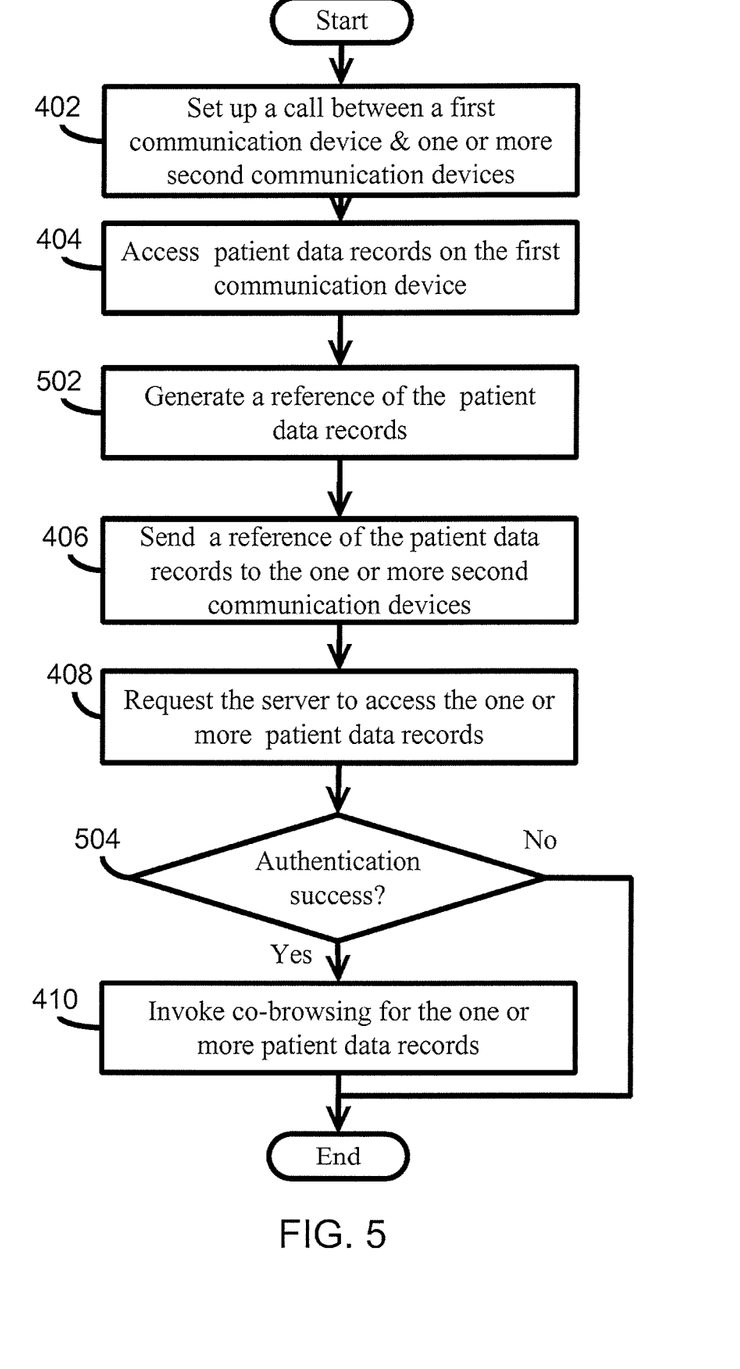
FIG. 5 shows a flow chart of a method for co-browsing of patient records on communication devices, in accordance with another embodiment of the present invention.

FIG. 5 shows a flow chart of a method for co-browsing of patient records on communication devices, in accordance with another embodiment of the present invention. At step 402, the system 200 sets up a communication session between the first communication device 102 and the one or more second communication devices 104, 106, 108 and 110, where the communication is initiated by the first communication device 102. At step 404, the first communication device 102 accesses one or more patient data records on a server. In an embodiment of the present invention, the server authenticates the first communication device 102 before providing an access to the one or more patient data records. At step 502, the server generates a reference of the one or more patient data records. The server provides a reference of the one or more patient data records to the first communication device 102. At step 406, the first communication device 102 sends the reference of the one or more patient data records to the one or more second communication devices 104, 106, 108 and 110. At step 408, at least one of the one or more second communication devices 104, 106, 108 and 110 requests the server to access the one or more patient data records, where the request includes the reference of the one or more patient data records. In an embodiment of the present invention, the server authenticates the at least one of the one or more second communication devices 104, 106, 108 and 110 before providing an access to the one or more patient data records. At step 504, the server authenticates the reference received from the at least one of the one or more second communication devices 104, 106, 108 and 110. Finally, at step 410, the system 200 invokes the co-browsing for the one or more patient data records, where the co-browsing is provided during the communication session.

In an embodiment of the present invention, the system 200 closes the access to the one or more patient data records to the at least one of the one or more second communication devices 104, 106, 108 and 110 when the communication session is closed.

In another embodiment of the present invention, the system 200 continues providing the access to the one or more patient data records to the at least one of the one or more second communication devices 104, 106, 108 and 110 after the communication session is closed.

Figure 6:
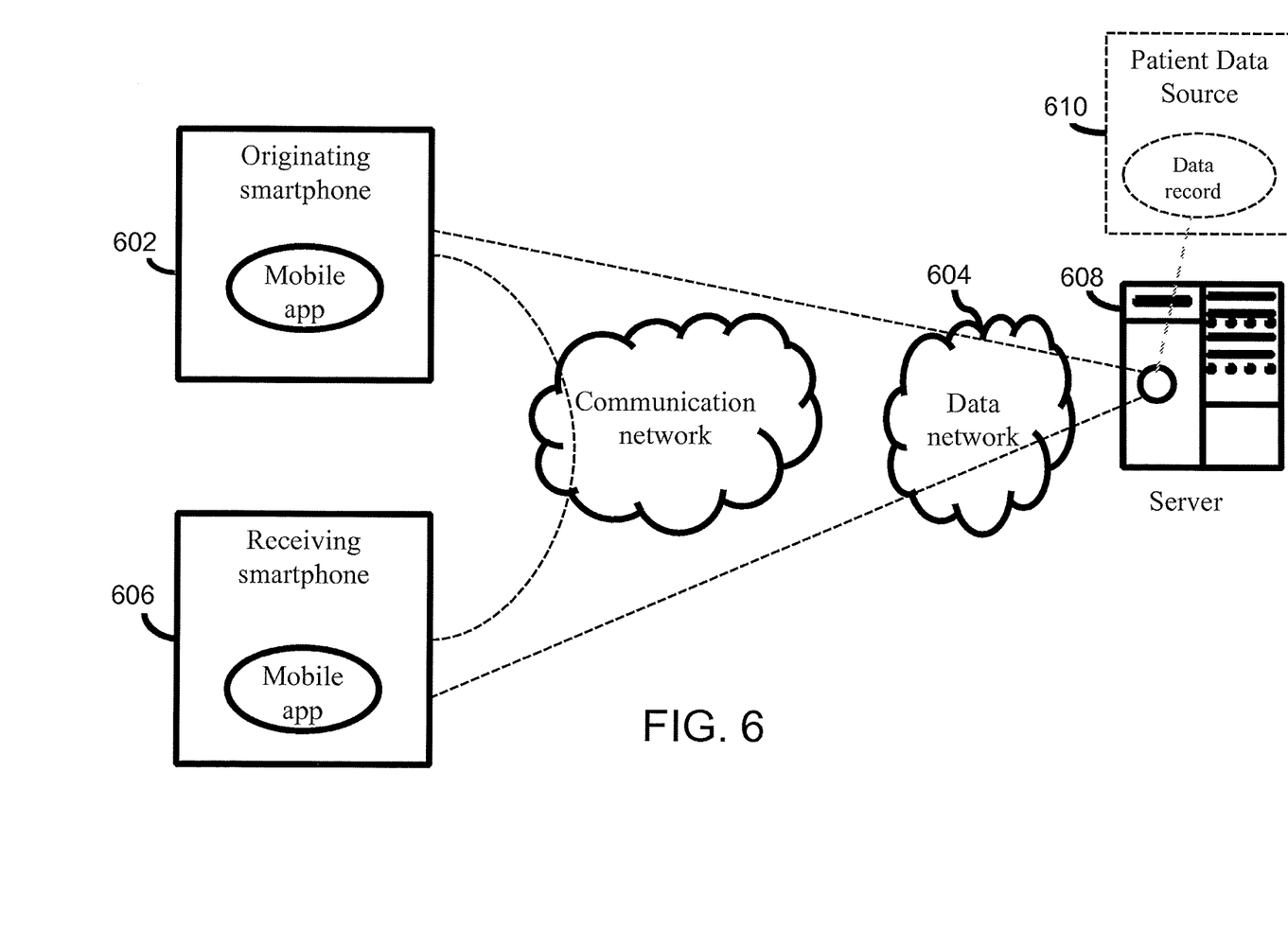
FIG. 6 shows architecture of a system for co-browsing of patient records on communication devices, in accordance with an embodiment of the present invention.

FIG. 6 shows architecture of a system for co-browsing of patient records on communication devices, in accordance with an embodiment of the present invention. The patient records can be co-browsed during a communication session by clinicians or by clinicians and patients. An originating smartphone 602 uses the data network 604, to establish communication sessions with a receiving smartphone 606. The originating smartphone 602 then accesses a server 608 to look up data it needs to share with the receiving smartphone 606. In an embodiment of the present invention, the server 608 is connected to a patient data source repository 610 of the patient data records. Examples of such repositories include, but are not limited to, an EMR, an EHR and a PHR. In an embodiment of the present invention, the server 608 exchanges data with the patient data source repository 610 using medical data exchange standards. Examples of such standards include, but are not limited to, Health Level Seven (HL7) standards, Electronic Health Record Communication (EN 13606) standards and Health Informatics Service Architecture (HISA) standards. In an embodiment of the present invention, the server 608 is connected to the central repository via secure APIs. In an embodiment of the present invention, the data exchange between smartphones and the server 608 and the data exchange between the server 608 and the patient data record repository 610 is encrypted and never persistently stored on the server 608 or the devices 602 and 606. Examples of the encryption technologies include, but are not limited to, SSL, IPSec and algorithms such as symmetric key cryptography algorithms, public key cryptography algorithms. In an embodiment of the present invention, the server 608 follows Health Insurance Portability and Accountability Act (HIPAA) guidelines for patient privacy and information security, to securely handle the Protected Health Information (PHI). The method is designed to specifically eliminate any need for the server 608 and the devices 602 and 608 to store any information that is received from the patient data source repository 610.

The applications on originating smartphone 602 access the data from the server 608 and display to a user. The server 608 authenticates the originating smartphone 602 before providing access to the patient data. The server 608 then interacts with the patient data source repository 610 to provide access to the patient data. The user can then invoke a communication session while the application accesses the patient data records from the server 608. Then the originating smartphone 602 sends location information (reference) of the data on the server 608 to the receiving smartphone 606. The communication session, specifically protocols like SIP, can carry reference of the patient data records as part of the signaling fields and/or message headers. Depending on the specific signaling protocol used and the information it can carry, the reference can range from being as simple as a small number acting as an ID of that record to even a full URL pointing to the data record. The server component mediates the sharing by dynamically generating such references and then resolving them to the actual patient data records when it receives a request for that ID in context of that call (voice/video session). The extracted reference is used to fetch the data record information from the server 608 to display to a user of the receiving smartphone 606. The receiving smartphone 606 then fetches the data from the server 608 and displays to the user of the receiving smartphone 606.

Figure 7:
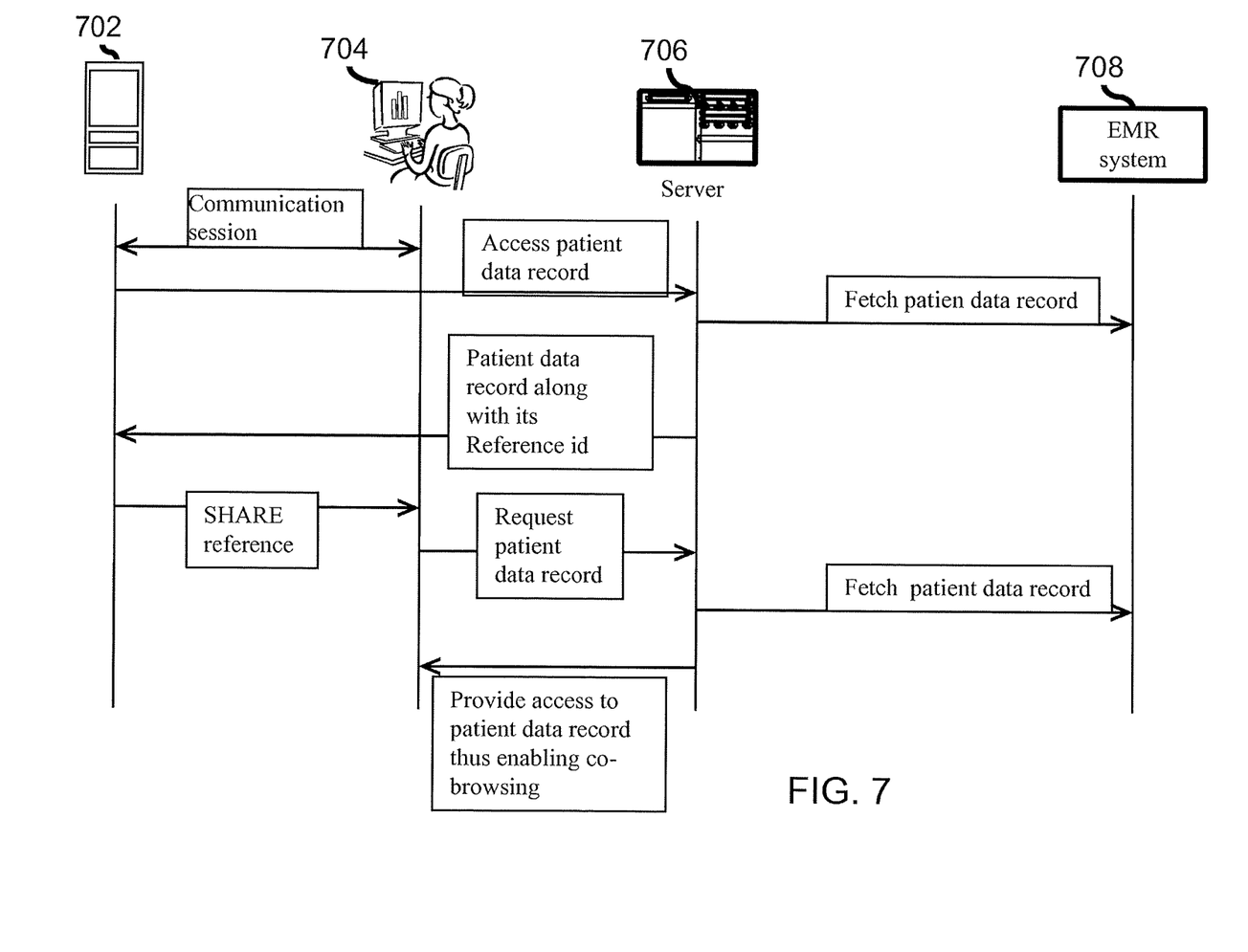
FIG. 7 shows a sample process for co-browsing of patient records on communication devices, in accordance with an embodiment of the present invention.

FIG. 7 shows a sample process for co-browsing of patient records on communication devices, in accordance with an embodiment of the present invention. Two users, User A and User B, use communication devices such as a smartphone or a tablet computer. User A launches an application on mobile device 702 implementing the mechanism of this invention to start a call with User B. The application installed on the user A's mobile device 702 makes phone calls over the communication network to user B's device 704 running the same application. The application uses the communication network to initiate the call. In an embodiment of the present invention, the call is setup through the communication network using the communication signaling protocol (e.g. Session Initiation Protocol—SIP) supported by that network. In response to the incoming call, User B's device 704 launches the same application and user B answers the call through that application.

At this time any of these two users, can use the application to browse some patient data records on the server 706 via a data network. The server 708 fetches the patient data records from an EMR system 708. Along with the record's data, the server 706 sends the dynamically generated record ID to the User's application. The server maintains a mapping between that ID and the actual data record. In the present embodiment, User A starts browsing the patient data records. The mobile application on the mobile device 702 interacts with the server 706 to browse the patient data records stored on the EMR system 708. The mobile application on the mobile device 702 accesses the server 706 over a data communication service available to the mobile device 702. The application fetches specific patient data records from the server 706 by sending the IDs of the patient data records. User A then selects the action on the application to share that patient data record with User B. The application uses the signaling protocol to pass the patient data record ID to the User B's application. This involves sending a signaling message (such as SIP INFO) which carries this ID information. On receiving this signaling message, the User B's application extracts the patient data record ID and sends a request to the server 706 to fetch the patient data record with that ID. The server 706 looks up the mapping at the EMR system 708 to determine the record corresponding to that ID and sends the records data to the User B's application where it is displayed to the user on the device 704. In this way the two users can bring up any records in any arbitrary order to share with the other user.

Figure 8:
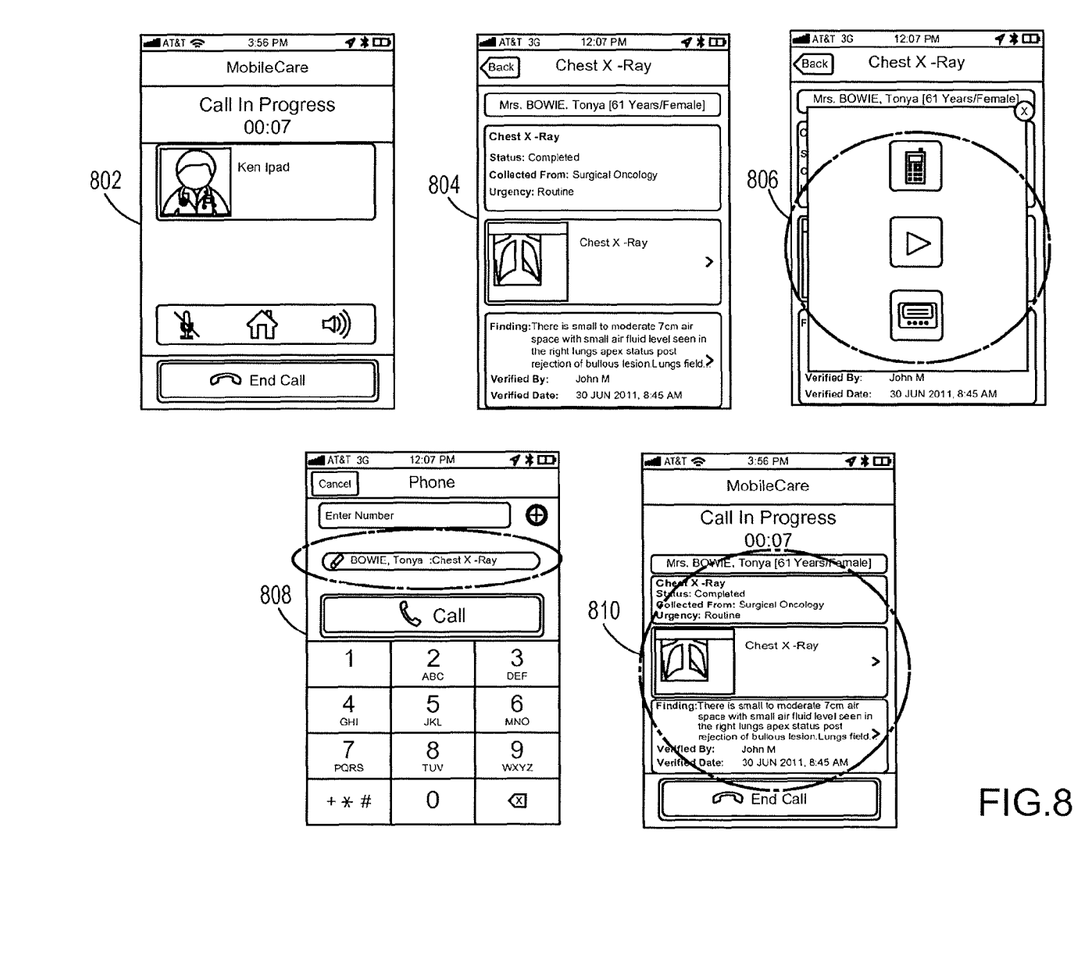
FIG. 8 shows an example of sharing patient records, in accordance with an embodiment of the present invention.

FIG. 8 shows an example of co-browsing patient records, in accordance with an embodiment of the present invention. At screen 802, user A initiates a call with a user at the other end point. At screen 804, an application on user A's device fetches a patient record from the server. The user A can be a clinician or a patient to whom the patient record belongs. The server authenticates the user A before providing access to the patient record. In the present embodiment, the patient record is a Chest X-ray result record. Further, at screen 806, on the application, user A invokes a communication dialog, and selects phone call as the mode of communication. Further, at screen 808, the application records the patient record reference (id and location on the server) and makes it ready for transmission to the other endpoint via the communications signaling protocol. In the present embodiment, the record is shared with a clinician at the other end point. The record reference is sent via the signaling protocol to the other end point as the phone call is initiated by the application. Finally, at screen 810, the user at the other end point is able to view the same patient record, as shared by the user A during the communication session. This invention matches this need and the enabling technology to provide a novel way for the physicians and nurses to co-browse patient data for improved outcomes in patient care.

Additionally, the concepts of this invention are quite generic in nature and can be applied in variety of ways. In simple terms it allows two or more end-points connected to each other in any way to share data stored on a third commonly shared resource. This can be applied to go over slides presentations in a conference call. The slides would be sent to the server by the presenter at the beginning of the call, and then fetched one slide at a time by the users watching the presentation as the presenter advances slides from his device-forward, backward or jumps to any specific slide. In a similar way it can be used to implement a solution to view pictures together among friends and family. Further, the invention allows a concurrent and bi-directional control on bringing-up a data record for co-browsing.

Additionally, the invention can be applied to areas where the endpoints are not smartphones, but any devices with small computing power, such as embedded software systems. The present invention brings the voice, video and co-browsing on such devices by utilizing a different paradigm of the voice, video, data sharing based collaboration. In addition to the streaming of voice and video, it introduces the concept of co-browsing by sharing the reference of the data rather than the data itself. So as the users interact via streaming media, they are also able to send reference of different pieces of data back and forth among the users. The data itself is available on a server accessible to all the users' devices. The application on the mobile devices automatically fetches the data indexed by the reference that it receives from other users and displays it to the user. Thus users are able to have a co-browsing session in which they can share any kind of data and be able to discuss it in real-time.

The present invention utilizes the inherent capabilities in communication session signaling to pass on information. This mechanism is leveraged to send reference of (link to) data objects managed by a server accessible to both ends of the communication session. Such servers can be deployed in the cloud for global accessibility or the servers can be deployed within an enterprise LAN for secure access to enterprise users only. The server can be a proxy, an adaptor or an aggregator for the data sources, such as applications in the IT infrastructure of the enterprise or publicly accessible services on the Internet.

The present invention is implemented via software routines on the smartphone as well as on the server. The smartphone devices can be running operating systems such as Blackberry, iOS, Android, and Windows. Data communication service such as cellular 3G or Wi-Fi has to be available on the smartphone, via which the smartphone and the server can exchange information. The software performs the tasks of initiating media sessions among the smartphones, as well as accessing the data from the server and passing on the location of the data on the server to the receiving smartphone. The server hosts the content which would be shared in the collaboration session.

While the present invention has been described in connection with preferred embodiments, it will be understood by those skilled in the art that variations and modifications of the preferred embodiments described above may be made without departing from the scope of the invention. Other embodiments will be apparent to those skilled in the art from a consideration of the specification or from a practice of the invention disclosed herein. It is intended that the specification and the described examples are considered exemplary only, with the true scope of the invention indicated by the following claims.

What is claimed is:

1. A method for co-browsing of patient records during a communication session on a plurality of communication devices, the method comprising:
　initiating, at a first communication device, the communication session between the first communication device and one or more second communication devices;
　during the communication session, requesting, by the first communication device, a reference generated by a server and that is associated with one or more patient data records stored on the server;
　accessing, at the first communication device, the one or more patient data records by selecting the reference;
　sending, by the first communication device, the reference of the one or more patient data records to the one or more second communication devices;

requesting access to the one or more patient data records by at least one of the one or more second communication devices by selecting the reference of the one or more patient data records;

authenticating, by the server, each of the first communication device and the one or more second communication devices before providing access of each communication device to the one or more patient data records; and invoking co-browsing of the one or more patient data records, the co-browsing being provided during the communication session, wherein the co-browsing is being performed by the first communication device and the one or more second communication devices.

2. The method as recited in claim 1, wherein the one or more patient data records comprises one or more of demographic data, medical history, family history, imaging reports, laboratory test results, medications, dosing, prescription records, surgeries records, vaccination data, observations of daily living (ODLs) and clinical information.

3. The method as recited in claim 1, wherein the one or more patient records is part of one of an electronic medical record system (EMR), an electronic health record system (EHR) and a personal health record system (PHR).

4. The method as recited in claim 1, wherein the communication session takes place using a communication protocol.

5. The method as recited in claim 4, wherein the communication protocol is one of Session Initiation Protocol (SIP), Extensible Messaging and Presence Protocol (XMPP), Session Description Protocol (SDP), Inter-Asterisk exchange (IAX), H.323 protocol, Media Gateway Control Protocol (MGCP), Signaling System #7 (SS7), Integrated Services Digital Network (ISDN), Plain Old Telephone Service (POTS) protocol and a voice over Internet Protocol (VoIP) protocol.

6. The method as recited in claim 1 further comprising: sending, by the first communication device, the reference via one of a signaling message, push notification, multi-media message (MMS), a SMS and an Email.

7. The method as recited in claim 1, wherein the communication devices include one or more of a desktop, a laptop, a mobile phone, a tablet PC, a netbook, an e-book reader, an embedded computing device, and a PDA.

8. The method as recited in claim 1, wherein the communication session is created over one of Internet, 3G, 4G, and local area network (LAN).

9. The method as recited in claim 1, wherein the server is one of a web server, a server cloud, a proxy server, a local server, and a LAN server.

10. The method as recited in claim 1, wherein the server provides access to the one or more patient data records without storing the one or more patient data records, the server being one of a proxy of the patient data records, an adaptor of the patient data records, and an aggregator of the patient data records.

11. The method as recited in claim 1, wherein the reference comprises one or more of link to the patient data records, a record ID, an authentication information and a session token.

12. The method as recited in claim 1 further comprising: authenticating, at the server, the reference received from the at least one of the one or more second communication devices.

13. The method as recited in claim 1, wherein the co-browsing is one of synchronous browsing and asynchronous browsing.

14. The method as recited in claim 1 further comprising: prohibiting access of the at least one of the one or more second communication devices to the one or more patient data records when the communication session is complete.

15. The method as recited in claim 1 further comprising: providing continued access to the at least one of the one or more second communication devices to the one or more patient data records after the communication is complete.

16. A system for co-browsing during a communication session on a plurality of communication devices, the system comprising:

a first communication device configured to:
  initiate a communication session with one or more second communication devices,
  during the communication session, transmit a request to a server to generate a reference associated with one or more patient data records stored on the server,
  access the one or more patient data records via a server by selecting the reference, and
  send the reference of the one or more patient data records to the one or more second communication devices; and the one or more second communication devices being configured to access the one or more patient data records by selecting the reference received from the first communication device, wherein the server is configured to:
  authenticate the first communication device and the one or more second communication devices before providing access of each communication device to the one or more patient data records, and
  invoke co-browsing of the one or more patient data records during the communication session, wherein the co-browsing is being performed by the first communication device and the one or more second communication devices.

17. The system as recited in claim 16, wherein the one or more patient data records comprises one or more of demographic data, medical history, family history, imaging reports, laboratory test results, medications, dosing, prescription records, surgeries records, vaccination data, observations of daily living (ODLs) and clinical information.

18. The system as recited in claim 1, wherein the one or more patient records is part of one of an electronic medical record system (EMR), an electronic health record system (EHR) and a personal health record system (PHR).

19. The system as recited in claim 16, wherein the communication session takes place using a communication protocol.

20. The system as recited in claim 19, wherein the communication protocol is one of Session Initiation Protocol (SIP), Extensible Messaging and Presence Protocol (XMPP), Session Description Protocol (SDP), Inter-Asterisk exchange (IAX), H.323 protocol, Media Gateway Control Protocol (MGCP), a voice over Internet Protocol (VoIP) protocol, a traditional telephony signalling and media protocol, Signaling System #7 (SS7), Integrated Services Digital Network (ISDN), and Plain Old Telephone Service (POTS) protocols.

21. The system as recited in claim 16, wherein the reference module sends the reference via one of a signaling message, push notification, multi-media message (MMS), a SMS and an Email.

22. The system as recited in claim 16, wherein the plurality of communication devices include one or more of a desktop, a laptop, a mobile phone, a tablet PC, a netbook, an e-book reader, an embedded computing device and a PDA.

23. The system as recited in claim 16, wherein the communication session is created over one of Internet, 3G, 4G and local area network (LAN).

24. The system as recited in claim 16, wherein the server is one of a web server, a server cloud, a proxy server, a local server and a LAN server.

25. The system as recited in claim 16, wherein the server provides access to the one or more patient data records without storing the one or more patient data records, the server being one of a proxy of the patient data records, an adaptor of the patient data records, and an aggregator of the patient data records.

26. The system as recited in claim 16, wherein the reference comprises one or more of link to the patient data records, a record ID, an authentication information and a session token.

27. The system as recited in claim 16, wherein the server is further configured to
authenticate the reference received from the at least one of the one or more second communication devices.

28. The system as recited in claim 16, wherein the co-browsing is one of synchronous co-browsing and asynchronous co-browsing.

29. The system as recited in claim 16, wherein the server is further configured to
prohibit access of the at least one of the one or more second communication devices to the one or more patient data records when the communication session is complete.

30. The system as recited in claim 16, wherein the server is further configured to
provide continued access to the at least one of the one or more second communication devices to the one or more patient data records after the communication is complete.

* * * * *